(12) United States Patent
Shimuta (10) Patent No.: US 11,828,662 B2
(45) Date of Patent: Nov. 28, 2023

(54) ELECTRONIC DEVICE

(71) Applicant: Murata Manufacturing Co., Ltd., Nagaokakyo (JP)

(72) Inventor: Toru Shimuta, Nagaokakyo (JP)

(73) Assignee: MURATA MANUFACTURING CO., LTD., Nagaokakyo (JP)

(*) Notice: Subject to any disclaimer, the term of this patent is extended or adjusted under 35 U.S.C. 154(b) by 722 days.

(21) Appl. No.: 16/918,780

(22) Filed: Jul. 1, 2020

(65) Prior Publication Data
US 2020/0333195 A1    Oct. 22, 2020

Related U.S. Application Data

(63) Continuation of application No. PCT/JP2019/000646, filed on Jan. 11, 2019.

(30) Foreign Application Priority Data

Jan. 12, 2018 (JP) ................. 2018-003130

(51) Int. Cl.
*G01K 7/22* (2006.01)
*G01K 1/024* (2021.01)
(Continued)

(52) U.S. Cl.
CPC .............. *G01K 7/22* (2013.01); *G01K 1/024* (2013.01); *G01K 1/14* (2013.01); *H05K 1/181* (2013.01);
(Continued)

(58) Field of Classification Search
CPC ............ G01K 7/22; G01K 1/024; G01K 1/14; G01K 2215/00; G01K 13/20; G01K 13/25;
(Continued)

(56) References Cited

U.S. PATENT DOCUMENTS 9,183,738 B1 * 11/2015 Allen, Sr. ............... G01K 13/20
2004/0200699 A1   10/2004 Matsumoto et al.
(Continued)

FOREIGN PATENT DOCUMENTS

JP    S63146926 U    9/1988
JP    H0581959 A     4/1993
(Continued)

OTHER PUBLICATIONS

International Search Report issued for PCT/JP2019/000646, dated Apr. 10, 2019.
(Continued)

*Primary Examiner* — Brandi N Hopkins
*Assistant Examiner* — Janice M Soto
(74) *Attorney, Agent, or Firm* — ArentFox Schiff LLP (57) ABSTRACT

A core body thermometer that includes a wiring substrate on which a power supply switch and electronic components are mounted. The power supply switch is housed so as to face a back surface of an upper exterior body in a space formed by the upper exterior body and a lower exterior body. Moreover, a lining member is formed in a thin plate shape and disposed on the back surface of the upper exterior body, and a buffer member is disposed between the wiring substrate and the lining member. The lining member has a through-hole in which the power supply switch is placed in an inner side in a thickness direction when viewed in a plan view, and has flexibility in an operation direction of the power supply switch).

18 Claims, 9 Drawing Sheets

(51) Int. Cl.
*G01K 1/14* (2021.01)
*H05K 1/18* (2006.01)
*H05K 7/14* (2006.01)

(52) U.S. Cl.
CPC ....... *H05K 7/1427* (2013.01); *G01K 2215/00* (2013.01); *H05K 2201/10053* (2013.01)

(58) Field of Classification Search
CPC ............ G01K 1/16; G01K 1/08; H05K 1/181; H05K 7/1427; H05K 2201/10053; H01H 9/04; H01H 13/06; A61B 5/01
USPC .......................................................... 600/549
See application file for complete search history.

(56) References Cited

U.S. PATENT DOCUMENTS

| | | | |
|---|---|---|---|
| 2014/0275932 A1* | 9/2014 | Zadig ................. | A61B 5/02438 |
| | | | 600/386 |
| 2017/0055896 A1* | 3/2017 | Al-Ali .................... | A61B 5/318 |
| 2017/0178833 A1 | 6/2017 | Mizuno et al. | |
| 2018/0028072 A1* | 2/2018 | Shi ....................... | A61B 5/6833 |

FOREIGN PATENT DOCUMENTS

| | | |
|---|---|---|
| JP | H05205561 A | 8/1993 |
| JP | 2001082007 A | 3/2001 |
| JP | 2004327430 A | 11/2004 |
| JP | 2008235226 A | 10/2008 |
| JP | 2017117593 A | 6/2017 |

OTHER PUBLICATIONS

Written Opinion of the International Searching Authority issued for PCT/JP2019/000646, dated Apr. 10, 2019.

* cited by examiner

ELECTRONIC DEVICE

CROSS REFERENCE TO RELATED APPLICATIONS

The present application is a continuation of PCT/JP2019/000646 filed Jan. 11, 2019, which claims priority to Japanese Patent Application No. 2018-003130, filed Jan. 12, 2018, the entire contents of each of which are incorporated herein by reference.

TECHNICAL FIELD

The present invention relates to an electronic device, and more particularly, to an electronic device having waterproof properties.

BACKGROUND

Depending on the application, waterproof properties may be required for an electronic device. In the electronic device being required such waterproof properties, the waterproof properties are required also for an operation switch for receiving a user operation. For example, Patent Document 1 (identified below) discloses an electronic device with a button operable in water.

More specifically, the electronic device in Patent Document 1 includes a substrate main body having a first surface and a second surface that face away from each other, a dome switch arranged on the first surface, a waterproof sheet arranged so as to include a portion covering the dome switch, and an adhesive layer arranged on at least a part of the waterproof sheet. The waterproof sheet is stuck to a base portion or another member by an adhesive layer so as to form a watertight space including the dome switch.

Patent Document 1: Japanese Unexamined Patent Application Publication No. 2017-117593.

According to the above-described electronic device, there is no water around the dome switch, and there is no risk of ingress of water into the dome switch. Therefore, it is possible to operate the button in water. However, when electronic components and the like are mounted around the dome switch, a pressing force may be applied to the electronic components and the like when the dome switch is pressed. Therefore, when stress is applied to the electronic components and the like and the stress is repeated, failure (e.g., fault) such as breakage of the electronic components and the like, poor contact, and the like, may occur.

SUMMARY OF THE INVENTION

The exemplary embodiments of the present invention have been made in order to solve the above-described problems. Thus, it is an object of the present invention to provide an electronic device configured to reduce stress applied to electronic components mounted on a wiring substrate when an operation switch is operated. The electronic device has waterproof properties inside which the wiring substrate on which the operation switch, the electronic components, and the like are mounted is housed.

In an exemplary aspect, an electronic device is provided that includes an upper exterior body made of a material having waterproof properties; a lower exterior body that makes close contact with the upper exterior body at a peripheral edge portion and forms a space together with the upper exterior body; and a wiring substrate on which an operation switch and electronic components are mounted. Moreover, the operation switch is arranged so as to face the upper exterior body in the space; a lining member is disposed between the upper exterior body and the wiring substrate; and a buffer member is disposed between the wiring substrate and the lining member. The lining member is characterized in that it has a first aperture in which the operation switch is placed in an inner side when viewed in a plan view, and is bent in an operation direction of the operation switch.

According to the electronic device of the exemplary embodiment, the peripheral edge portion of the upper exterior body made of the material having waterproof properties and the peripheral edge portion of the lower exterior body are made in close contact with each other. Moreover, the wiring substrate on which the operation switch and the electronic component are mounted is housed therein (e.g., in a sealed space formed by the upper exterior body and the lower exterior body), so that waterproof properties are provided with a relatively simple structure. On the other hand, the lining member is disposed on a back surface of the upper exterior body, and the buffer member is disposed between the wiring substrate and the lining member, so that a shape of the upper exterior body can be held and deformation can be suppressed. In addition, when the operation switch is operated, the lining member bends in the operation direction (for example, a pressing direction) of the operation switch to receive the pressing force caused by the switch operation of a user and the buffer member is compressively deformed. Therefore, the pressing force associated with the switch operation by the user can be absorbed. As such, the stress applied to the electronic components can also be reduced. Further, when the operation of the operation switch is finished, the bent lining member and the deformed buffer member return to their original shapes, and thus the outer shape of the upper exterior body can be restored. It is also noted that in the lining member, since a first aperture in which the operation switch is placed in the inner side is formed in a plan view, the operation switch can be easily operated from the outer side of the upper exterior body by a fingertip. As a result, in the electronic device having the waterproof properties inside which the wiring substrate on which the operation switch, the electronic components, and the like are mounted is housed, the stress applied to the electronic components mounted on the wiring substrate when the operation switch is operated can also be reduced.

According to the exemplary embodiments of the present invention, in an electronic device having waterproof properties inside which a wiring substrate on which an operation switch, electronic components, and the like are mounted is housed, stress applied to the electronic components mounted on the wiring substrate when the operation switch is operated can be reduced.

DETAILED DESCRIPTION OF EMBODIMENTS

Hereinafter, exemplary embodiments of the present invention will be described in detail with reference to the accompanying drawings. It is noted that in the drawings, the same or corresponding parts will be denoted by using the same reference numerals. Further, in each drawing, the same elements are denoted by the same reference numerals, and redundant description thereof will be omitted. Note that, here, a non-heating type core body thermometer (hereinafter simply referred to as "core body thermometer") will be described as an example of an electronic device according to the present invention.

Figure 1:
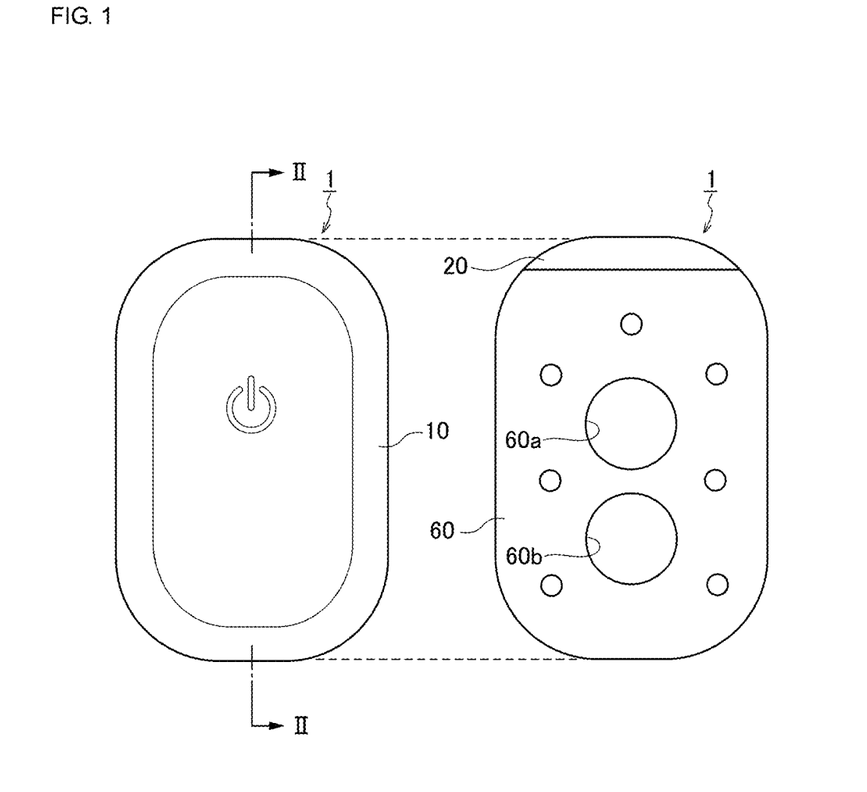
FIG. 1 includes a plan view and a bottom view illustrating an appearance of a core body thermometer according to an exemplary embodiment.
Figure 2:
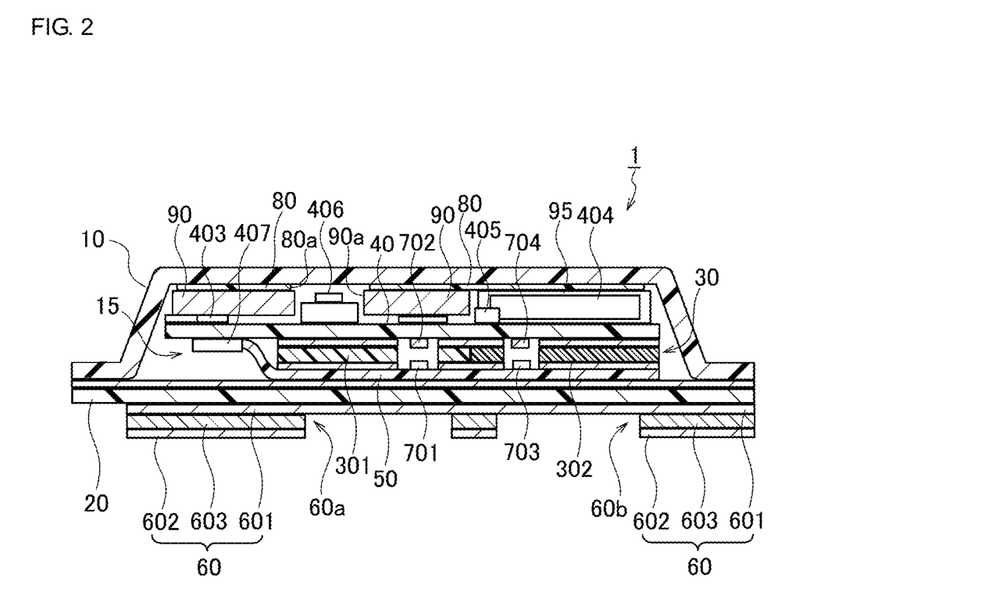
FIG. 2 is a cross-sectional view illustrating a configuration of the core body thermometer according to the exemplary embodiment.
Figure 3:
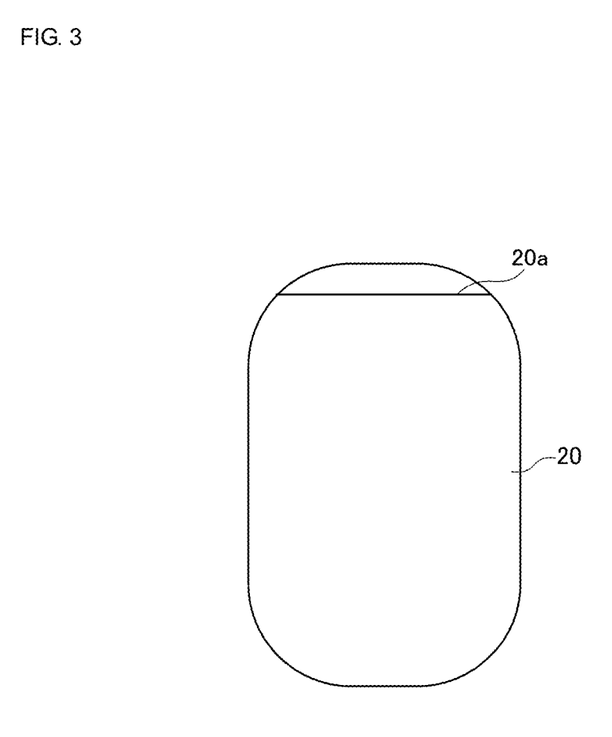
FIG. 3 is a plan view illustrating a lower exterior body configuring the core body thermometer according to the exemplary embodiment.
Figure 4:
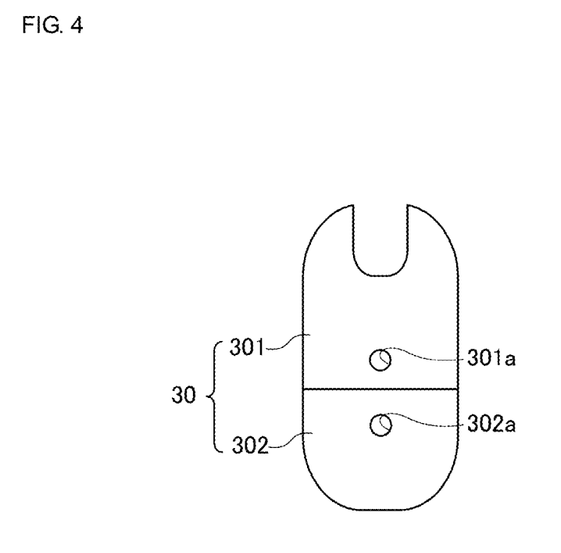
FIG. 4 is a plan view illustrating a thermal resistor layer configuring the core body thermometer according to the exemplary embodiment.
Figure 5:
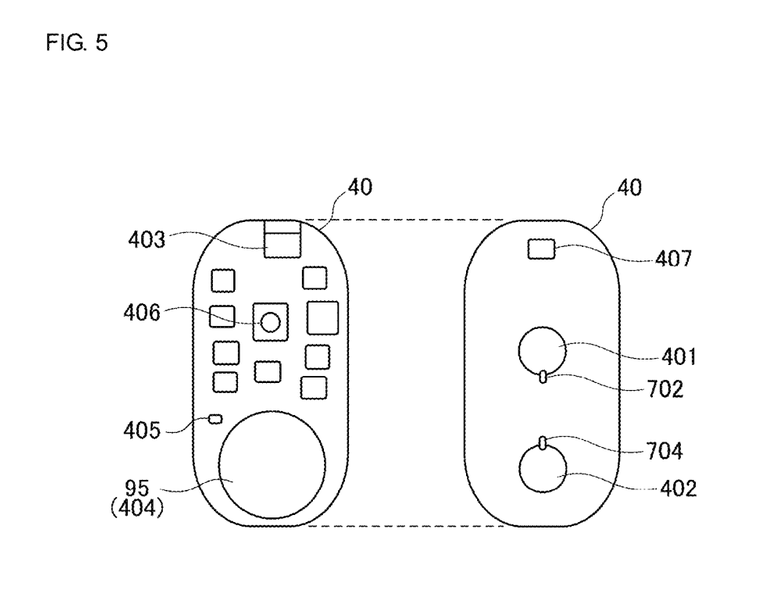
FIG. 5 includes a plan view and a bottom view illustrating a wiring substrate configuring the core body thermometer according to the exemplary embodiment.
Figure 6:
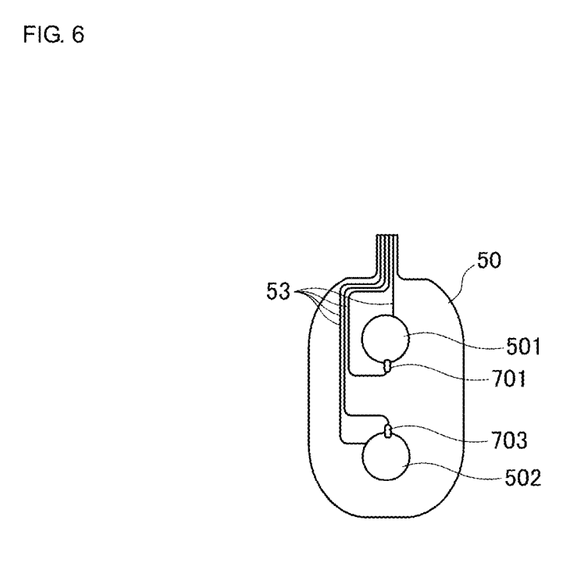
FIG. 6 is a plan view illustrating a flexible substrate configuring the core body thermometer according to the exemplary embodiment.
Figure 7:
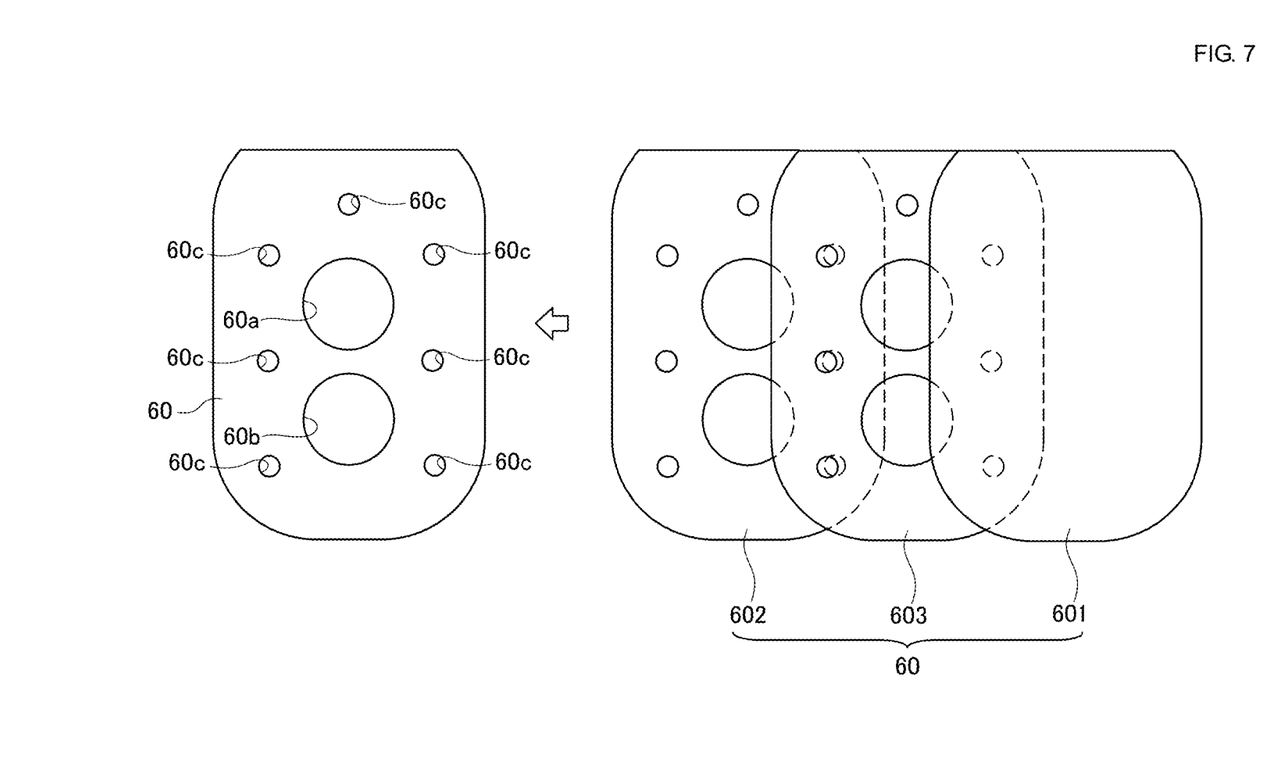
FIG. 7 includes a plan view and an exploded view illustrating a sticking member configuring the core body thermometer according to the exemplary embodiment.

First, a configuration of a core body thermometer 1 according to the exemplary embodiment will be described with reference to FIG. 1 to FIG. 7. FIG. 1 includes a plan view and a bottom view illustrating an appearance of the core body thermometer 1. FIG. 2 is a cross-sectional view illustrating the configuration of the core body thermometer 1 (cross-sectional view taken along a line II-II in FIG. 1). FIG. 3 is a plan view illustrating a lower exterior body 20 configuring the core body thermometer 1. FIG. 4 is a plan view illustrating a thermal resistor layer 30 configuring the core body thermometer 1. FIG. 5 includes a plan view and a bottom view illustrating a wiring substrate 40 configuring the core body thermometer 1. FIG. 6 is a plan view illustrating a flexible substrate 50 configuring the core body thermometer 1. FIG. 7 includes a plan view and an exploded view illustrating a sticking member 60 configuring the core body thermometer 1.

The core body thermometer 1 is a non-heating type core body thermometer that obtains heat flow rates from a core body of a measurement subject based on a difference between temperatures detected by a first temperature sensor 701 and a second temperature sensor 702 and a difference between temperatures detected by a third temperature sensor 703 and a fourth temperature sensor 704, and acquires a core body temperature. Further, the core body thermometer 1 is a sticking-type core body thermometer that is stuck to a body surface of the measurement subject (i.e., a person) and continuously measures the body temperature to acquire body temperature data. In particular, the core body thermometer 1 is a core body thermometer having waterproof properties inside which the wiring substrate 40 on which a power supply switch 406, electronic components, and the like are mounted is housed. Thus, a core body thermometer is provided that is configured to reduce stress applied to the electronic components mounted on the wiring substrate 40 when the power supply switch 406 is operated.

The core body thermometer 1 is configured to mainly include an upper exterior body 10, the lower exterior body 20, a body temperature measurement unit 15, a lining member 80, a buffer member 90, and the sticking member 60. Further, the body temperature measurement unit 15 is configured to mainly include the thermal resistor layer 30, the wiring substrate 40 on which the second temperature sensor 702 and the fourth temperature sensor 704 are mounted, and the flexible substrate 50 on which the first temperature sensor 701 and the third temperature sensor 703 are mounted. Hereinafter, each element of the core body thermometer 1 will be described in detail.

The upper exterior body 10 is made of, for example, a foamed material with closed cells or semi-closed cells having waterproof properties and heat retaining properties. In order to prevent the temperature of the body temperature measurement unit 15 from being locally changed due to a sudden change in an ambient air temperature, it is preferable to use a foamed material having a low thermal conductivity for the upper exterior body 10. It is noted that as a material, for example, polyurethane, polystyrene, polyolefin, or the like is preferably used. Further, as a processing method of the upper exterior body 10, for example, vacuum molding is preferably used. The upper exterior body 10 is formed to have a substantially hat-shaped cross section so as to house the body temperature measurement unit 15 (the thermal resistor layer 30, the wiring substrate 40, the flexible substrate 50, and the like). Therefore, a side surface of the thermal resistor layer 30 is covered with the foamed material, and the side surface of the thermal resistor layer 30 is prevented from being exposed to the ambient air.

The lower exterior body 20 is formed of, for example, a non-foamed resin film having waterproof properties and a higher thermal conductivity than that of the upper exterior body 10. Examples of the material include polypropylene, polyethylene, polyester, polyimide, and the like, and in particular, polyethylene terephthalate is preferably used. The lower exterior body 20 is formed in a planar shape in a manner such that the flexible substrate 50 (body temperature measurement unit 15) to which the first temperature sensor 701 and the third temperature sensor 703 are attached can be fixed in a close contact manner. It is noted that, since a gap formed between the body temperature measurement unit 15 and the lower exterior body 20 causes thermal resistance to vary and this influences a heat flux, it is preferable that the body temperature measurement unit 15 and the lower exterior body 20 be fixed in a close contact manner by a method of bonding with a double-sided adhesive tape, a method of fixing with an adhesive, or the like. The upper exterior body 10 and the lower exterior body 20 are formed to have the same or substantially the same sizes (i.e., the outer dimensions), and are formed to have sizes of, for example, 40 to 100 mm in a longitudinal direction and 20 to 60 mm in a lateral direction, for example.

Then, a peripheral edge portion of the upper exterior body 10 having the substantially hat-shaped cross section and a peripheral edge portion of the lower exterior body 20 formed in the planar shape are fixed in a close contact manner by, for example, bonding with a double-sided adhesive tape, fixing with an adhesive, heat sealing, or the like. It is noted that, in order to achieve waterproof performance, it is desirable that a portion where the upper exterior body 10 and the lower exterior body 20 are fixed in a close contact manner be flat and have a structure in which wrinkles are less likely to be formed. That is, it is preferable that an outer edge portion of the lower exterior body 20 be flat, an outer edge portion of the opposing upper exterior body 10 be also flat, and those outer edge portions be stuck to each other and fixed in a close contact manner. In this way, since force is uniformly applied to the close-contact fixed portion, the problem, such as generation of wrinkles, that the waterproof performance is adversely affected hardly occurs.

As illustrated in FIG. 2, the body temperature measurement unit 15 is configured by laminating the flexible substrate 50, the thermal resistor layer 30, and the wiring substrate 40 in this order from the lower exterior body 20 side.

The thermal resistor layer 30 includes two thermal resistors having different thermal resistance values. That is, a first thermal resistor 301 and a second thermal resistor 302, in order to form two heat fluxes (see FIG. 4). As the first thermal resistor 301, a material having a higher thermal conductivity (i.e., a lower thermal resistance value) than that of the second thermal resistor 302, for example, plastic such as polypropylene, polyethylene, acrylic, polycarbonate, epoxy resin, and the like is preferably used. As the second thermal resistor 302, a material having a lower thermal conductivity (i.e., a higher thermal resistance value) than that of the first thermal resistor 301, for example, a foamed plastic (e.g., foam material) such as polyurethane, polystyrene, polyolefin, and the like is preferably used. However, plastic, rubber, and the like that are not foamed may also be used. Note that, here, the thermal conductivity of the metal such as copper and aluminum is equal to or more than 100 [W/m/K], whereas the thermal conductivity of the plastic such as polypropylene, polyethylene, acrylic, polycarbonate, epoxy resin, and the like is about 0.1 to 0.5 [W/m/K], and is smaller by about three orders of magnitude. The thermal conductivity of the foamed plastic is even smaller by almost one order of magnitude. The thermal conductivity of the air is even smaller and is 0.024 [W/m/K]. The first thermal resistor 301 and the second thermal resistor 302 are formed to have substantially the same thickness in order to achieve reduction in cost by enabling laminating with the wiring substrate 40 and the flexible substrate 50.

As further shown in FIG. 4, a first through-hole 301a passing through in a thickness direction is formed in the first thermal resistor 301 configuring the thermal resistor layer 30. Similarly, a second through-hole 302a passing through in the thickness direction is formed in the second thermal resistor 302 configuring the thermal resistor layer 30. The first through-hole 301a is formed in a manner such that the first temperature sensor 701 and the second temperature sensor 702 are placed in an inner side when viewed in a plan view. In other words, the first temperature sensor 701 and the second temperature sensor 702, which are paired, are arranged inside (i.e., in the inner side of) the first through-hole 301a along the thickness direction of the first thermal resistor 301. Similarly, the second through-hole 302a is formed in a manner such that the third temperature sensor 703 and the fourth temperature sensor 704 are placed in an inner side when viewed in a plan view. In other words, the third temperature sensor 703 and the fourth temperature sensor 704, which are paired, are arranged inside (i.e., in the inner side of) the second through-hole 302a along the thickness direction of the second thermal resistor 302.

Here, as the first temperature sensor 701 to the fourth temperature sensor 704 (hereinafter, also collectively referred to as "temperature sensor" or a "biological sensor" 70), for example, a thermistor, a temperature measuring resistor, or the like whose resistance value varies depending on temperature is preferably used. It is noted that each of the temperature sensors preferably has a small heat capacity as much as possible from the viewpoint of enhancing responsiveness. Therefore, a chip thermistor is preferably used. Each of the first temperature sensor 701 to the fourth temperature sensor 704 is electrically connected to a processing circuit, which will be described later, via a printed wiring, and an electric signal corresponding to the temperature is read by the processing circuit.

In order to reduce the size of the thermal flow-type core body thermometer 1, it is important to reduce the size of the thermal resistor layer 30. However, when the thermal resistor layer 30 is made small, a difference in output values of the paired temperature sensors becomes small, and thus measurement error may be increased. Here, since each of the temperature sensors 701-704 has a substantially rectangular parallelepiped shape and is thick, the thickness of the temperature sensors cannot be ignored when the thermal resistor layer 30 is made thinner. When each temperature sensors is in contact with the side surface of the thermal resistor layer 30, heat is transferred thereto from the contact portion, and therefore, the temperature of the respective temperature sensor may become a temperature deviating from the surface temperature of the thermal resistor layer 30. In order to reduce this influence, a structure is adopted in which the through-holes 301a and 302a are formed in the thermal resistor layer 30 around the respective temperature sensor, and the respective temperature sensor is not in contact with the side surface of the thermal resistor layer 30.

The wiring substrate 40 as shown in FIG. 5 is, for example, a rigid substrate such as a glass epoxy substrate. On the wiring substrate 40, there is mounted the processing circuit configured for processing the output signals of the first temperature sensor 701 to the fourth temperature sensor 704 to acquire core body temperature data. In addition, a wireless communication unit 403 that transmits the acquired core body temperature data, and a coin battery 404 that supplies electric power to the processing circuit and the wireless communication unit 403 are mounted on the wiring substrate 40. The processing circuit mainly includes a temperature input circuit and an arithmetic processing circuit. The temperature input circuit is configured to include, for example, an amplifier such as an operational amplifier, an analog/digital converter, and the like (corresponding to electronic components for purposes of this disclosure) for reading a detection signal of the temperature sensors 701-704. The temperature input circuit amplifies an analog signal output from the temperature sensors 701-704, converts the amplified analog signal into a digital signal, and outputs the digital signal to the arithmetic processing circuit.

The arithmetic processing circuit is configured to calculate the core body temperature from the read measurement (i.e., temperature) data. The arithmetic processing circuit is formed by, for example, a micro control unit (MCU), an EEPROM, a RAM, and the like (corresponding to the electronic components for purposes of this disclosure), and calculates the core body temperature based on the detected values of the temperature sensors 701-704, which have been read by the temperature input circuit. In addition, the arithmetic processing circuit is configured to store the calculated core body temperature data in a memory such as the RAM or the like. Further, the arithmetic processing circuit outputs the calculated core body temperature data to the wireless communication unit 403, thereby wirelessly outputting the calculated core body data to an external device in an exemplary aspect.

It is noted that, here, the arithmetic processing circuit is configured to calculate (e.g., to estimate) the core body temperature based on the temperature differences between the front and back surfaces of the thermal resistors 301 and 302, which are caused by a difference between the two heat fluxes formed by using the two thermal resistors 301 and 302 having different thermal resistances. More specifically, the arithmetic processing circuit calculates a core body temperature Tb based on, for example, the following equation (1).

$$Tb=\{T1(T3-T4)*Ra1-T3(T1-T2)*Ra2\}/\{(T3-T4)*Ra1-(T1-T2)*Ra2\} \qquad (1)$$

It is noted that Tb represents the core body temperature, T1 represents a temperature detected by the first temperature sensor 701, T2 represents a temperature detected by the second temperature sensor 702, and Ra1 represents a thermal resistance value of the first thermal resistor 301. Further, T3 represents a temperature detected by the third temperature sensor 703, T4 represents a temperature detected by the fourth temperature sensor 704, and Ra2 represents a thermal resistance value of the second thermal resistor 302.

Here, since Ra1 and Ra2 are known, the core body temperature Tb can be uniquely obtained by detecting four temperatures (T1, T2, T3, T4).

On a lower surface of the wiring substrate 40, the second temperature sensor 702 that acquires the temperature of an upper surface (e.g., ambient air side) of the first thermal resistor 301, and the fourth temperature sensor 704 that detects the temperature of an upper surface (e.g., ambient air side) of the second thermal resistor 302 are mounted. More specifically, thermal equalization patterns 401 and 402 for equalizing temperature distribution of surroundings are formed on the lower surface of the wiring substrate 40, one electrode of the second temperature sensor 702 is connected to the thermal equalization pattern 401, and one electrode of the fourth temperature sensor 704 is connected to the thermal equalization pattern 402. The thermal equalization patterns 401 and 402 are made of, for example, a material having a high thermal conductivity, such as a metal film.

In order to prevent only the temperature of a part of the wiring substrate 40 from being changed due to influences of the ambient air temperature and the like, it is preferable to provide an equalization member having a high thermal conductivity for thermally equalizing the influences of the temperature distribution of the ambient air temperature on a rear side (e.g., ambient air side) of a wiring layer on which the second temperature sensor 702 and the fourth temperature sensor 704 are mounted. Here, as the equalization member, a metal foil, a metal thin plate, or the like may be used, but as similar to the wiring layer formed on the wiring substrate 40, it is desirable to form the equalization member as a wiring pattern of an inner layer of the wiring substrate 40. In this case, the wiring pattern of the inner layer, which is used as the equalization member, may be a ground pattern, but is preferably an independent pattern which is not connected to an electric circuit and through which no current flows.

According to the exemplary aspect, the wireless communication unit 403 is configured to transmit the acquired core body temperature data to an external management device, an information terminal (for example, a smartphone or the like). Here, the wireless communication unit 403 transmits the core body temperature data to the external management device or the information terminal, for example, by using Bluetooth (registered trademark) or the like. The thin coin battery 404 supplies electric power to the electronic components of the above-described processing circuit, the wireless communication unit 403, and the like. The coin battery 404 is housed in a battery holder 95 mounted on (i.e., attached to) the wiring substrate 40. The battery holder 95 is disposed between the wiring substrate 40 and the lining member 80, and is configured to function as a spacer member. That is, the battery holder 95 also serves as the spacer member that supports the lining member 80. It is noted that, in order to reduce a sticking area of the body temperature measurement unit 15 to the measurement subject, and to prevent influence of heat generation caused by change in the ambient air temperature and operations of the wireless communication unit 403, the wireless communication unit 403 and the coin battery 404 (the battery holder 95) are disposed on the side (i.e., the upper surface side) opposite to the temperature sensors 701-704 with the wiring substrate 40 interposed therebetween.

On an upper surface of the wiring substrate 40, the power supply switch 406 (corresponding to an operation switch) that receives an ON/OFF operation of a power supply by the measurement subject with the upper exterior body 10 interposed therebetween is mounted. The wiring substrate 40 is housed in a sealed space formed by the upper exterior body 10 and the lower exterior body 20 in a manner such that the power supply switch 406 faces the back surface (i.e., the rear surface) of the upper exterior body 10. As the power supply switch 406, for example, a push button switch, a rocker switch, or the like is preferably used. It is noted that, in a case of the push button switch, the push button switch for alternate operation of holding an ON state even when a fingertip is released therefrom is preferably used. Further, as the power supply switch 406, a surface mount type is preferable, but a lead type may also be used.

Here, in order to prevent the power supply switch 406 from being erroneously pressed to turn ON/OFF the power supply, and to prevent the power supply switch 406 from pushing up the upper exterior body 10, the power supply switch 406 is disposed so as not to make contact with the upper exterior body 10. To be more specific, a gap between a button upper surface of the power supply switch 406 and the back surface of the upper exterior body 10 is preferably set to a range of, for example, 0 to 4 mm, and more preferably set to a range of 0.5 to 1.5 mm. In addition, the stroke of the power supply switch 406 is preferably set to a range of 0.1 to 1 mm, and more preferably set to a range of 0.1 to 0.3 mm, for example.

On the upper surface of the wiring substrate 40, an LED 405 that lights or flickers in accordance with a user's operation and a measurement state (for example, ON/OFF of the power supply switch 406, start/end of measurement, and the like) is mounted. It is noted that, instead of the LED, for example, a VCSEL or the like may be used. Further, an FPC connector 407 for electrically connecting the flexible substrate 50 is attached to the lower surface side of the wiring substrate 40.

According to an exemplary aspect, the flexible substrate 50 is made of, for example, polyimide, polyester, or the like, and has flexibility. On the flexible substrate 50, the first temperature sensor 701 that acquires the temperature of the first thermal resistor 301 on a skin side and the third temperature sensor 703 that acquires the temperature of the second thermal resistor 302 on the skin side are mounted. More specifically, as illustrated in FIG. 6, in order to equalize the temperature distribution of surroundings, thermal equalization patterns 501 and 502 are formed on the flexible substrate 50, one terminal of the first temperature sensor 701 is connected to the thermal equalization pattern 501, and one terminal of the third temperature sensor 703 is connected to the thermal equalization pattern 502. The thermal equalization patterns 501 and 502 are made of, for example, a material having a high thermal conductivity, such as a metal film. Each of the first temperature sensor 701 and the third temperature sensor 703 is connected to the wiring substrate 40 (e.g., a processing circuit) via a wiring pattern 53 and the above-described FPC connector 407, and electric signal corresponding to the temperature is read by the processing circuit. As described above, the lower exterior body 20, the flexible substrate 50, the thermal resistor layer 30, and the wiring substrate 40 are fixed in a close contact manner by, for example, a double-sided adhesive tape or the like so as to form no gap therebetween in order to form the heat fluxes.

The lining member 80 formed in a thin plate shape thinner than the buffer member 90, which will be described later, is disposed on the back surface of the upper exterior body 10, that is, between the upper exterior body 10, and the buffer member 90 and the battery holder (i.e., the spacer member) 95. In order to suppress wrinkles on the upper exterior body 10, the lining member 80 is attached to the upper exterior body 10 by sticking one surface of the lining member 80 to the back surface (i.e., the rear surface) of the upper exterior body 10 by, for example, a double-sided adhesive tape or the like. The lining member 80 is made, for example, of a resin material such as PET having flexibility, so as to be bendable in the operation direction of the power supply switch 406. Note that the lining member 80 may be formed of a thin metal plate or the like. Here, it is preferable to use PET as the lining member 80, but it is also possible to use plastic such as polycarbonate, polyimide, acrylic, polypropylene, and epoxy, a metal plate such as SUS, and aluminum, and the like in addition to PET. However, it is required to be a thin plate having a strength.

In the lining member 80, a through-hole 80a (corresponding to a first aperture for purposes of this disclosure) in which the power supply switch 406 is placed in an inner side when viewed in a plan view is formed in the thickness direction. It is noted that a circumference of the through-hole 80a may be completely closed or may not be completely closed. The through-hole 80a of the lining member 80 is formed to have such a size that it is smaller than a width of the fingertip so as not to cause the whole fingertip to enter the through-hole 80a, and a pad of the fingertip is inserted so as to press the power supply switch 406. More specifically, since the width of the fingertip differs from person to person, a maximum width of an opening of the through-hole 80a is preferably set to a range of, for example, 10 to 20 mm, and more preferably set to a range of 13 to 16 mm. When the upper exterior body 10 is thick (for example, equal to or more than 2 mm), an inner diameter of the through-hole 80a is preferably made larger in accordance with the thickness of the upper exterior body 10.

The buffer member 90 having buffering properties and formed in a plate shape is disposed between the upper surface of the wiring substrate 40 and the lining member 80. The buffer member 90 is formed to be thicker than a height of the power supply switch 406 mounted on the wiring substrate 40 from a mounting surface of the wiring substrate 40 and heights of the electronic components from the mounting surface of the wiring substrate 40. The buffer member 90 is attached to the lining member 80 by sticking to another surface of the lining member 80 by, for example, a double-sided adhesive tape or the like. Here, as the buffer member 90, a foamed material or a foamed plastic can be used. More specifically, as the buffer member 90, polyurethane, polyolefin, polyethylene, polystyrene, polypropylene, EVA (ethylene-vinyl acetate copolymer), phenol, PET, and the like can be used. In particular, as the buffer member 90, it is preferable to use polyurethane. Preferably, the buffer member 90 is selected so as to be softer than the lining member 80 in a manner such that the electronic components mounted on the wiring substrate 40 are not broken or detached due to impact. Further, it is preferable that the buffer member 90 be made sufficiently thicker (e.g., equal to or more than two times) than the electronic components mounted on the wiring substrate 40.

In the buffer member 90, a through-hole (corresponding to a second aperture for purposes of this disclosure) 90a in which the power supply switch 406 is placed in an inner side when viewed in a plan view is formed in the thickness direction. The through-hole 90a formed in the buffer member 90 is formed and disposed so as to be placed in the inner side of the through-hole 80a formed in the lining member 80 when viewed in a plan view. That is, the through-hole 90a of the buffer member 90 is formed to be smaller than the through-hole 80a of the lining member 80. Further, each of the through-hole 90a formed in the buffer member 90 and the through-hole 80a formed in the lining member 80 is formed in a circular shape or a substantially circular shape (including an oval shape, or the like, for example), and the maximum width of each opening is formed to be smaller than the width of the fingertip. More specifically, the maximum width of the through-hole 90a of the buffer member 90 is preferably set to a range of, for example, 8 to 18 mm, and more preferably set to a range of 11 to 14 mm. It is noted that, in a case where the upper exterior body 10 is thick (for example, equal to or more than 2 mm), an inner diameter of the through-hole 90a is preferably made larger in accordance with the thickness thereof.

As illustrated in FIG. 7, the sticking member 60 includes a first adhesive layer 601 to be stuck to a surface of an outer side of the lower exterior body 20, a breathable ventilation layer 603 (that is, a moisture permeable layer that allows moisture to pass therethrough) to be stuck to the first adhesive layer 601, and a second adhesive layer 602 to be stuck to the ventilation layer 603. In a case where the core body thermometer 1 is stuck to the skin for use, sweat accumulated between the skin and the core body thermometer 1 for a long time may cause the skin to be inflamed. However, by providing the ventilation layer 603 that allows moisture to pass in the sticking member 60, stuffiness by sweat or the like is suppressed. As the ventilation layer 603, for example, a non-woven fabric can be suitably used. It is noted that a woven or knitted fabric may be used instead of the non-woven fabric. Further, paper, wood, sponge/open-cell foamed material, or the like may be used, or plastic, rubber, or a metal structure having a groove or a hole extending from the center of the body temperature measurement unit 15 toward a peripheral edge thereof may be used.

Since the ventilation layer 603 contains the air therein, the thermal conductivity thereof is usually low. Therefore, when the ventilation layer 603 is positioned between the skin and the sensors, the body temperature measurement accuracy is affected. In order to stably measure the body temperature, the ventilation layer 603 is not arranged in a region overlapping with the first temperature sensor 701 and the third temperature sensor 703, which measure the temperature of the skin, and the thermal equalization patterns 501 and 502 connected to them.

Here, a case where the non-woven fabric is used as the ventilation layer 603 will be described as an example. As illustrated in FIG. 7, double-sided adhesive tapes (i.e., the first adhesive layer 601 and second adhesive layer 602) having biocompatibility are stuck to both sides of the non-woven fabric. In the ventilation layer 603 and the second adhesive layer 602, through-holes 60a and 60b, in which the first temperature sensor 701 and the third temperature sensor 703 are placed in inner sides are formed in the thickness direction when viewed in a plan view. Here, it is preferable that no through-hole be formed in the double-sided adhesive tape to be stuck to the lower exterior body 20 (i.e., the first adhesive layer 601). This is because when the through-hole is formed therein, the area of the first adhesive layer 601 decreases, and therefore the contact area between the lower exterior body 20 and the skin decreases, and it becomes difficult to closely contact with the skin, and the measurement accuracy may be lowered.

Further, in general, since the double-sided adhesive tape (i.e., the second adhesive layer 602) is inferior in the moisture permeability to the non-woven fabric, it is preferable to form a plurality of (e.g., seven in the example illustrated in FIG. 7) through-holes 60c formed in the thickness direction in at least the second adhesive layer 602. In that case, for example, it is preferable to arrange the through-holes 60c having a diameter of about 1 to 10 mm with distances of about 2 to 20 mm. It is noted that, instead of the through-hole 60c, for example, a notch having a crossing portion may be formed. In that case, it is preferable to arrange the intersecting notches having a length of about 1 to 10 mm with distances of about 2 to 20 mm.

Figure 8:
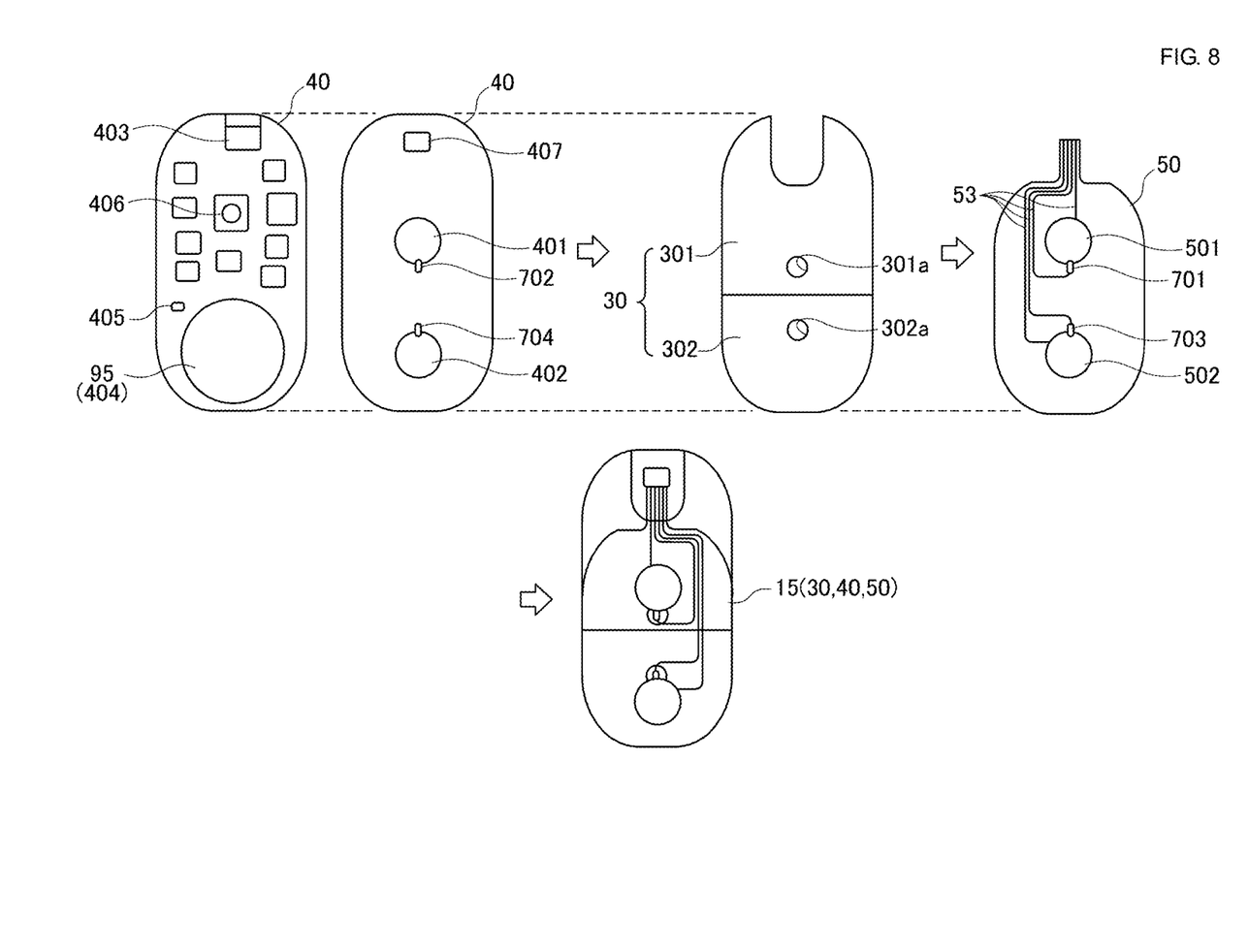
FIG. 8 is a diagram (part 1) for explaining a method of assembling the core body thermometer according to the exemplary embodiment.
Figure 9:
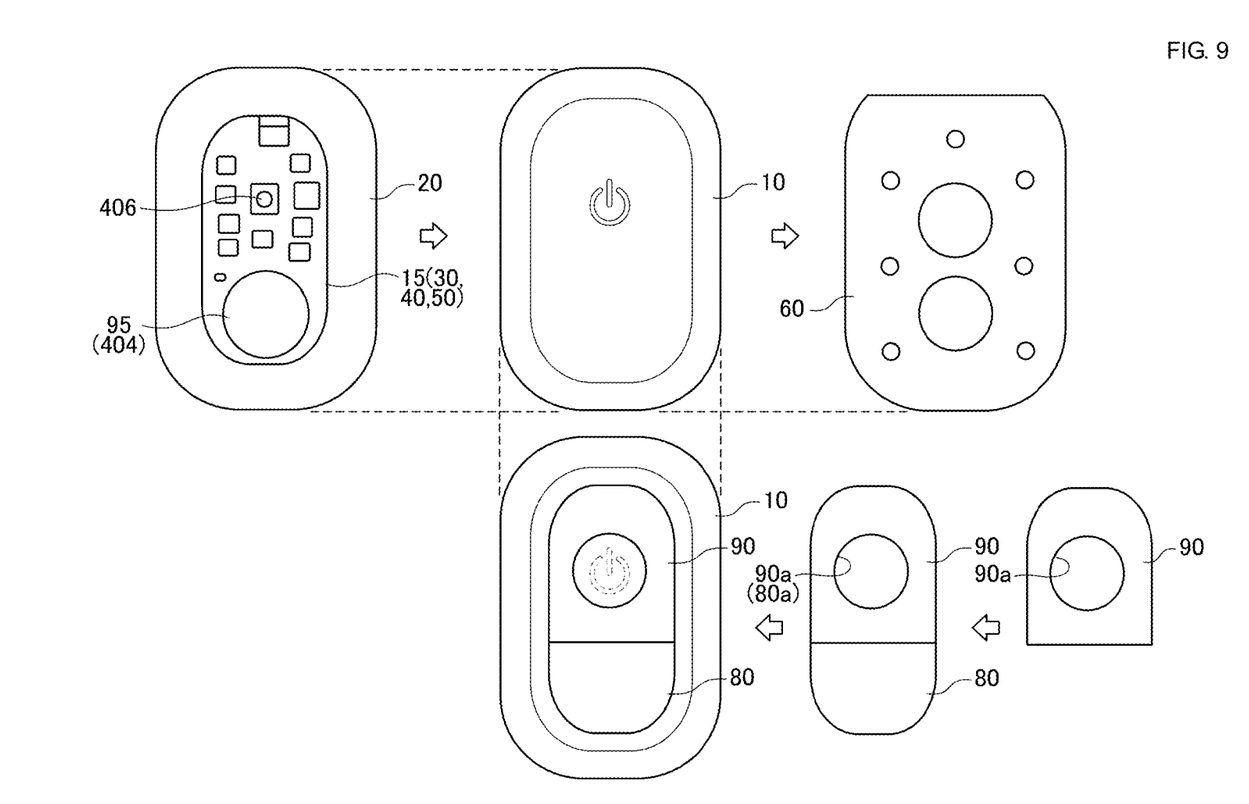
FIG. 9 is a diagram (part 2) for explaining the method of assembling the core body thermometer according to the exemplary embodiment.

Next, a method of assembling the core body thermometer 1 (manufacturing method) will be described with reference to FIG. 8 and FIG. 9. FIG. 8 is a diagram (part 1) for explaining the method of assembling the core body thermometer 1. FIG. 9 is a diagram (part 2) for explaining the method of assembling the core body thermometer 1.

The core body thermometer 1 is assembled, for example, in the following steps (1) to (7).

One surface of the thermal resistor layer 30 (the first thermal resistor 301 and the second thermal resistor 302) is fixed to the back surface of the wiring substrate 40 in a close contact manner by a double-sided adhesive tape.

After the flexible substrate 50 is connected to the FPC connector 407 of the wiring substrate 40, the flexible substrate 50 is fixed to another surface of the thermal resistor layer 30 in a close contact manner by a double-sided adhesive tape.

The coin battery 404 is fitted to the wiring substrate 40.

The flexible substrate 50 side of the body temperature measurement unit 15 is fixed to a central portion of the lower exterior body 20 in a close contact manner by a double-sided adhesive tape.

One surface of the lining member 80 is stuck to the back surface of the upper exterior body 10 by a double-sided adhesive tape, and the buffer member 90 is stuck to another surface of the lining member 80 by a double-sided adhesive tape.

The peripheral edge portion of the upper exterior body 10 to which the lining member 80 and the buffer member 90 are stuck and the peripheral edge portion of the lower exterior body 20 to which the body temperature measurement unit 15 is fixed are fixed in a close contact manner with a double-sided adhesive tape.

The sticking member 60 is stuck to a bottom surface of the lower exterior body 20. As described above, the core body thermometer 1 is then assembled. It is noted that, in the present embodiment, since the first temperature sensor 701 and the third temperature sensor 703 are not arranged at symmetrical positions from the center of the lower exterior body 20, a mark 20a for indicating a sticking direction of the sticking member 60 is put on the lower exterior body 20. The first temperature sensor 701 and the third temperature sensor 703 may be arranged at symmetrical positions from the center of the lower exterior body 20, and the mark 20a indicating the sticking direction of the sticking member 60 may be eliminated.

When the core body thermometer 1 assembled as described above is used, firstly, a separator attached to the second adhesive layer 602 of the sticking member 60 is peeled off. The separator prevents the second adhesive layer 602 from adhering to a portion other than the measurement subject before the core body thermometer 1 is used. Next, after the power supply switch 406 is pressed from an outer side of the upper exterior body 10 to turn ON the power supply, the second adhesive layer 602 is stuck to the measurement site of the measurement subject. It is noted that since the power supply switch 406 may be erroneously pressed during the measurement, it is preferable that an operation of turning ON/OFF the power supply be received by, for example, a long pressing of equal to or more than several seconds or by a plurality of pressing operations. When the operation is received, the LED 405 emits light in a predetermined light emission pattern, and informs the user that the operation has been accepted. When the power supply is turned ON, the core body temperature measurement, storage of the measurement data in the memory, and wireless data output are started. It is also note that when the core body temperature is measured, a measurement site is preferably the chest, the underarm, the back, the waist, the neck, the occipital, the forehead, but may be the abdomen, the flank, the thigh, the ankle, the arm, the wrist, or the like when body temperature fluctuation is measured.

As described in detail above, according to the present embodiment, the peripheral edge portion of the upper exterior body 10 formed from the foamed material with the closed cells or the semi-closed cells having the waterproof properties and the peripheral edge portion of the lower exterior body 20 formed of the non-foamed resin film are in close contact, and in the internal space thereof, the wiring substrate 40 on which the power supply switch 406 and the electronic components are mounted are housed, so that the waterproof properties can be exerted with a relatively simple structure. On the other hand, since the lining member 80 formed in the thin plate shape is disposed on the back surface of the upper exterior body 10 and the buffer member 90 having the buffering properties is disposed between the wiring substrate 40 and the lining member 80, the shape of the upper exterior body 10 having flexibility and made of the foamed material with the closed cells or the semi-closed cells can be held and the deformation can be suppressed. Further, when the power supply switch 406 is operated, the lining member 80 is bent toward the operation direction of the power supply switch 406, so that the pressing force caused by the switching operation of the measurement subject is received, and the buffer member 90 having the buffering properties is compressively deformed, so that the pressing force caused by the switch operation of the measurement subject can be absorbed. That is, it is possible to reduce the stress applied to the electronic components. Further, when the operation of the power supply switch 406 is finished, the bent lining member 80 and the deformed buffer member 90 return to the original shape, and thus it is possible to restore the outer shape of the upper exterior body 10. It is also noted that, in the lining member 80, since the through-hole 80a in which the power supply switch 406 is placed in an inner side is formed in the thickness direction in a plan view, the power supply switch 406 can be easily operated from the outer side of the upper exterior body 10 by the fingertip. As a result, in the core body thermometer 1 having waterproof properties inside which the wiring substrate 40 on which the power supply switch 406, the electronic components, and the like are mounted is housed, it is possible to reduce the stress applied to the electronic components mounted on the wiring substrate 40 when the power supply switch 406 is operated.

According to the present embodiment, the buffer member 90 is formed in the plate shape, and the through-hole 80a in which the power supply switch 406 is placed in the inner side is formed in the thickness direction in a plan view, and therefore, the power supply switch 406 can be easily operated. Further, it is possible to provide the user with an operational feeling of the power supply switch 406 more directly.

According to the present embodiment, the through-hole 90a formed in the buffer member 90 is formed and disposed so as to be placed in the inner side of the through-hole 80a formed in the lining member 80 in a plan view. Therefore, the lining member 80 and the upper exterior body 10 can be supported by the buffer member 90. Further, it is possible to disperse the pressing force applied to the upper exterior body 10 by the switch operation or the like of the measurement subject by the lining member 80 and the buffer member 90.

Moreover, according to the present embodiment, each of the through-hole 90a formed in the buffer member 90 and the through-hole 80a formed in the lining member 80 is formed in the substantially circular shape, and each of the inner diameters thereof is formed to be smaller than the outer diameter of the fingertip. As such, the fingertip can be prevented from entering the through-holes 80a and 90a, that is, the pressing force can be prevented from being applied to the electronic components without impairing operability of the power supply switch 406 when the power supply switch 406 is operated.

According to the present embodiment, since the lining member 80 is attached to the upper exterior body 10 by sticking one surface of the lining member 80 to the back surface of the upper exterior body 10, wrinkles are unlikely to be formed in the upper exterior body 10, and it is possible to add tension at the surface of the upper exterior body 10.

Furthermore, according to the present embodiment, since the buffer member 90 is attached to the lining member 80 by sticking to the other surface of the lining member 80, it is possible to prevent the buffer member 90 from being displaced. Further, since the buffer member 90 is stuck to the lining member 80 side, separation from the wiring substrate 40 is facilitated.

According to the present embodiment, since the power supply switch 406 is prevented from coming into contact with the back surface of the upper exterior body 10, the power supply switch 406 can be prevented from being erroneously pressed.

According to the present embodiment, since the buffer member 90 is formed to be thicker than the heights of the electronic components mounted on the wiring substrate 40 from the mounting surface of the wiring substrate 40, the electronic components are prevented from coming in direct contact with the lining member 80. Moreover, since the buffer member 90 compressively deforms and absorbs the pressing force caused by the switch operation, the stress applied to the electronic components can be reduced.

According to the present embodiment, since the battery holder 95 is disposed between the wiring substrate 40 and the lining member 80, the lining member 80 can be supported by the battery holder 95 in addition to the buffer member 90. That is, the battery holder 95 can be used (i.e., configured) as a spacer member.

According to the present embodiment, the wireless communication unit 403 that transmits the acquired core body temperature data to the external device is provided. Therefore, since a cable for connecting to the external device is not necessary, the waterproof processing for a cable extraction portion becomes unnecessary. Therefore, it is possible to further improve the waterproof properties with the relatively simple structure. Further, since the cable is not provided, behaviors of the measurement subject are less likely to be inhibited, and thus, it is possible to continuously measure the body temperature and the like for a long time.

It is noted that while the exemplary embodiments of the present invention have been described above, the present invention is not limited to the above-described embodiments, and various modifications can be made. For example, in the above-described embodiment, the present invention is applied to a two-heat flux-type core body thermometer as the example for description, but the present invention may be applied to a one-heat flux-type core body thermometer. In addition, the present invention can also be applied to thermometers other than the core body thermometer. Further, the present invention can also be applied to, for example, an electrocardiograph and an electronic device for measuring respiration and pulse.

It is also noted that the shape, the size, and the arrangement of each of the thermal resistor layer 30, the wiring substrate 40, the flexible substrate 50, the lining member 80, and the buffer member 90, the arrangement of the first temperature sensor 701 to the fourth temperature sensor 704, and the like described above are not limited to the above-described embodiments, and may be arbitrarily set according to, for example, the requirements of accuracy and the like. For example, the lining member 80 may be formed in a tray shape and stuck so as to wrap around the inner side surface of the upper exterior body 10. Further, the through-hole 90a of the buffer member 90 is not essential, and may not be formed.

REFERENCE SIGNS LIST

1 CORE BODY THERMOMETER
10 UPPER EXTERIOR BODY
15 BODY TEMPERATURE MEASUREMENT UNIT
20 LOWER EXTERIOR BODY
30 THERMAL RESISTOR LAYER
301 FIRST THERMAL RESISTOR
302 SECOND THERMAL RESISTOR
301a, 302a THROUGH-HOLE
40 WIRING SUBSTRATE
401, 402 THERMAL EQUALIZATION PATTERN
403 WIRELESS COMMUNICATION UNIT
404 COIN BATTERY
405 LED
406 POWER SUPPLY SWITCH (OPERATION SWITCH)
407 FPC CONNECTOR
50 FLEXIBLE SUBSTRATE
501, 502 THERMAL EQUALIZATION PATTERN
60 STICKING MEMBER
601 FIRST ADHESIVE LAYER
602 SECOND ADHESIVE LAYER
603 VENTILATION LAYER
60a, 60b THROUGH-HOLE
701, 702, 703, 704 TEMPERATURE SENSOR
80 LINING MEMBER
80a THROUGH-HOLE (FIRST APERTURE)
90 BUFFER MEMBER

90a THROUGH-HOLE (SECOND APERTURE)
95 BATTERY HOLDER (SPACER MEMBER)

The invention claimed is:

1. An electronic device comprising:
an upper exterior body comprising a waterproof material;
a lower exterior body that contacts the upper exterior body at a peripheral edge portion to form a space together with the upper exterior body;
a wiring substrate having an operation switch and at least one electronic component mounted thereon, with the operation switch being arranged to face the upper exterior body in the space;
a lining member disposed between the upper exterior body and the wiring substrate; and
a buffer member disposed between the wiring substrate and the lining member,
wherein the lining member comprises a first aperture with the operation switch disposed therein in an inner side when viewed in a plan view.

2. The electronic device according to claim 1, wherein the lining member is structurally configured to bend in an operation direction of the operation switch.

3. The electronic device according to claim 1, wherein the buffer member comprises a plate shape and includes a second aperture with the operation switch disposed therein in an inner side when viewed in the plan view.

4. The electronic device according to claim 3, wherein the second aperture is disposed in an inner side of the first aperture in the lining member when viewed in the plan view.

5. The electronic device according to claim 4, wherein each of the first and second apertures comprise a circular shape or a substantially circular shape.

6. The electronic device according to claim 1, wherein the lining member is attached to the upper exterior body by sticking a first surface of the lining member to a first surface of the upper exterior body facing the space.

7. The electronic device according to claim 6, wherein the buffer member is attached to the lining member by sticking to a second surface of the lining member that is opposite the first surface of the lining member.

8. The electronic device according to claim 1, wherein the operation switch is disposed so as not to contact with a surface of the upper exterior body that faces the space.

9. The electronic device according to claim 1, wherein the buffer member comprises a thickness that is greater than respective heights of the at least one electronic component mounted on the wiring substrate.

10. The electronic device according to claim 1, further including a spacer member disposed between the wiring substrate and the lining member.

11. The electronic device according to claim 10, wherein the spacer member is a battery holder configured to house a battery that supplies electric power to the at least one electronic component.

12. The electronic device according to claim 1, further comprising:
a sticking member having a first surface configured to be stuck to a surface of an outer side of the lower exterior body, and a second surface configured to be stuck to a body surface of a living body; and
a biological sensor configured to detect a biological signal from the living body.

13. The electronic device according to claim 12, wherein the biological sensor is a temperature sensor configured to detect a body temperature of the living body.

14. The electronic device according to claim 12, further comprising a wireless communication unit configured to wirelessly transmit biological information acquired by the biological sensor to an external device.

15. An electronic device comprising:
an upper exterior body coupled to a lower exterior body at respective peripheral edges to form a space therebetween;
a wiring substrate disposed in the space and extending in a horizontal direction of the electronic device;
an operation switch mounted on the wiring substrate and extending in a vertical direction of the electronic device to face the upper exterior body;
a lining member extending in the horizontal direction and disposed between the upper exterior body and the wiring substrate; and
a buffer member extending in the horizontal direction and disposed between the wiring substrate and the lining member,
wherein the lining member comprises a first aperture extending in the vertical direction with the operation switch disposed therein in an inner side when viewed in a plan view of the wiring substrate.

16. The electronic device according to claim 15, wherein the lining member is structurally configured to bend in an operation direction of the operation switch.

17. The electronic device according to claim 15, wherein the buffer member comprises a plate shape and includes a second aperture with the operation switch disposed therein in an inner side when viewed in the plan view of the wiring substrate.

18. The electronic device according to claim 17, wherein the second aperture is disposed in an inner side of the first aperture in the lining member when viewed in the plan view of the wiring substrate.

* * * * *